US00PP36446P2

(12) United States Plant Patent
Barnes

(10) Patent No.: US PP36,446 P2
(45) Date of Patent: Feb. 11, 2025

(54) ***BOUVARDIA* PLANT NAMED 'WNBVESRED24'**

(50) Latin Name: ***Bouvardia* hybrid**
Varietal Denomination: WNBVESRED24

(71) Applicant: WinGen, LLC, Mustang Ridge, TX (US)

(72) Inventor: Brent D. Barnes, Riverside, CA (US)

(73) Assignee: WinGen LLC, Campbell, CA (US)

( * ) Notice: Subject to any disclaimer, the term of this patent is extended or adjusted under 35 U.S.C. 154(b) by 0 days.

(21) Appl. No.: 18/541,360

(22) Filed: Dec. 15, 2023

(51) Int. Cl.
*A01H 5/02* (2018.01)
*A01H 6/76* (2018.01)

(52) U.S. Cl.
USPC ..... Plt./352

(58) Field of Classification Search
USPC ..... Plt./352
CPC ..... A01H 5/02; A01H 5/00; A01H 6/76
See application file for complete search history.

(56) References Cited

U.S. PATENT DOCUMENTS

PP34,579 P2 * 9/2022 Barnes ..... A01H 6/76
Plt./352

* cited by examiner

*Primary Examiner* — June Hwu
(74) *Attorney, Agent, or Firm* — Cassandra Bright

(57) ABSTRACT

A new and distinct cultivar of *Bouvardia* plant named 'WNBVESRED24' is disclosed, characterized by abundant, vivid, scarlet-red flowers. Plants are compact with good branching and habit. Good in-ground landscape performance with no lodging. The new cultivar is a *Bouvardia*, typically produced as an ornamental plant.

2 Drawing Sheets

Figure 1:
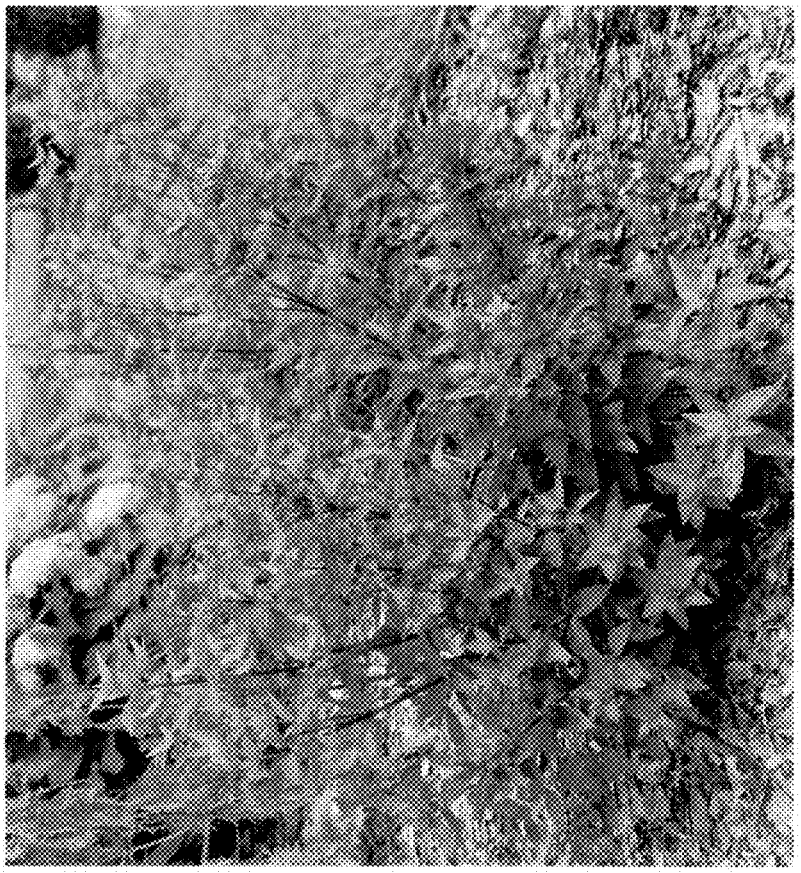

Latin name of the genus and species: *Bouvardia* hybrid. Cultivar denomination: 'WNBVESRED24'.

BACKGROUND OF THE INVENTION

The new *Bouvardia* cultivar is a product of a planned breeding program conducted by the inventor. The objective of the breeding program was to produce new *Bouvardia* cultivars with good landscape performance, strong branching and bloom coverage with some cut flower interest. The cross resulting in this new cultivar was made in September of 2015, at a research nursery in Bonsall, California.

The seed parent is an unnamed, unpatented variety of *Bouvardia* x *domestica*. The pollen parent is the unpatented, proprietary cultivar of *Bouvardia* hybrid referred to as '*Bouvardia* Texas #21'. The new cultivar was identified and selected as a potentially interesting selection in May of 2016 at the same nursery in Bonsall, California.

Asexual reproduction of the new cultivar 'WNBVESRED24' was first performed in May of 2016 in Bonsall, California, by tip cuttings. Subsequent propagation has shown that the unique features of this cultivar are stable and reproduced true to type in successive generations. Date of public disclosure was Jun. 27, 2023, occurring in Grand Haven, Michigan. This disclosure was made directly by the inventor or one who obtained the claimed invention directly or indirectly from the inventor. This sale and all public disclosures made between Jun. 27, 2023 and the filing of this application fall within the exception allowed under 102(b)(1).

SUMMARY OF THE INVENTION

The cultivar 'WNBVESRED24' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'WNBVESRED24'. These characteristics in combination distinguish 'WNBVESRED24' as a new and distinct *Bouvardia* cultivar:

1. Abundant, vivid scarlet-red flowers.
2. Compact shrub with good branching and habit.
3. Good in-ground landscape performance with no lodging.

PARENT COMPARISONS

Plants of the new cultivar 'WNBVESRED24' are similar to the seed parent in most horticultural characteristics. However, characteristics of the new cultivar differ in the following:

1. Flower color of the new cultivar is scarlet-red, while the flower color of the seed parent is pink with a fuchsia eye.
2. The new cultivar is a compact shrub suitable for landscape use, while the seed parent is a very compact cut flower plant suitable for pot production only.
3. The new cultivar blooms continuously from spring to summer, while the seed parent produces a single flush of blooms suitable for cut flower production.
4. Flowers of the new cultivar have no fragrance, while flowers of the seed parent have a noticeable fragrance.

Plants of the new cultivar 'WNBVESRED24' are similar to the pollen parent in most horticultural characteristics. However, characteristics of the new cultivar differ in the following:

1. Flower color of the new cultivar is scarlet-red, while the flower color of the pollen parent is orange.
2. The new cultivar is a compact shrub with good branching and habit, while the pollen parent is a medium-sized shrub with thinner branching.
3. The new cultivar blooms heavily and continuously from spring to summer, with larger flower clusters. The pollen parent blooms lightly and continuously from spring to summer, with fewer flowers per cluster.

COMMERCIAL COMPARISON

Plants of 'WNBVESRED24' are similar in some horticultural characteristics to the cultivar *Bouvardia ternifolia* 'Scarlet Hummer', unpatented. The new cultivar, however, differs in the following:

1. Plants of the new cultivar are more compact/tight than plants of this comparator.
2. The new cultivar is more floriferous than this comparator.

BRIEF DESCRIPTION OF THE PHOTOGRAPHS

The accompanying photograph in FIG. 1 illustrates in full color a typical plant of 'WNBVESRED24' grown in a field at a commercial nursery in Grand Haven, Michigan. This plant is 3 to 4 years old.

Figure 2:
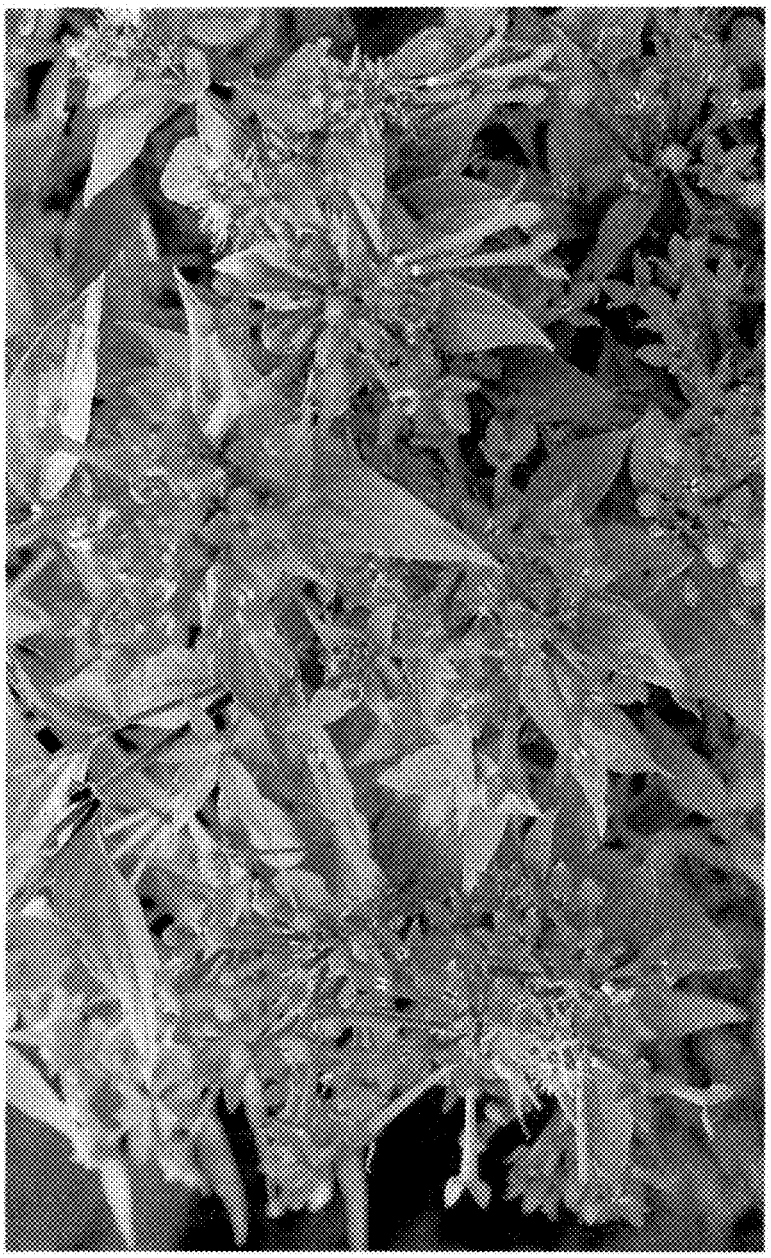

FIG. 2 illustrates a closer view of the flowers.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2015, except where general terms of ordinary dictionary significance are used. The following observations and measurements describe a 'WNBVESRED24' plant. This plant was grown in a field in Grand Haven, Michigan. The plant described is approximately 3 to 4 years old. Temperatures ranged from 0° to 29° C. during the day, and 10° C. to 12° C. at night. No artificial light, photoperiodic treatments were given to the plants. Measurements and numerical values represent averages of typical plant types.

Botanical classification: *Bouvardia* hybrid 'WNBVESRED24'.

PROPAGATION

Time to initiate roots: 5 to 7 days at approximately 18° C. to 27° C. in summer.

Time to produce a rooted plant: 4 weeks.

Root description: Sparse to moderate density of freely branching, thin, fibrous and fleshy roots. Tan in color, not effectively measured with a color chart.

PLANT

Plant type: Perennial shrub.

Age of plant described: Approximately 3 to 4 years old.

Plant shape: Upright and rounded.

Growth habit: Upwards and slightly outwards.

Height: 70 cm.

Plant spread: 75 cm.

Growth rate: Good.

Plant vigor: Quite vigorous.

Branching characteristics: Freely branching, some pinching required.

Length of lateral branches: 50 to 70 cm.

Diameter of lateral branches: 5 mm.

Quantity of lateral branches: About 30.

Internode length: 5 cm.

Stem:

- *Ramification*.—Weak.
- *Shape*.—Rounded.
- *Aspect*.—45° to 75°.
- *Strength*.—Strong, fairly rigid.
- *Color*.—New growth: RHS Yellow-Green 147C. Old Growth: RHS Greyed-Green 196A.
- *Pubescence*.—None.

FOLIAGE

Leaf:

- *Arrangement*.—Opposite.
- *Shape*.—Lanceolate.
- *Average length*.—6 cm.
- *Average width*.—3 cm.
- *Texture*.—Upper side: Glabrous. Under side: Glabrous with a pronounced midrib.
- *Apex*.—Acuminate.
- *Base*.—Cuneate.
- *Margin*.—Entire.
- *Durability to environmental stress*.—Excellent, high durability to wind and other stressors.
- *Color*.—Young, Upper side: RHS Green NN137B. Young, Under side: RHS Yellow-Green 147B. Mature, Upper side: RHS Green NN137B. Mature, Under side: RHS Yellow-Green 147B.
- *Venation*.—Type: Pinnate. Color: Upper side: RHS Yellow-Green 147C. Under side: RHS Yellow-Green 147C.

Petiole:

- *Length*.—5 mm.
- *Diameter*.—2 mm.
- *Color*.—Upper Surface: RHS Yellow-Green 147C. Lower Surface: RHS Yellow-Green 147C.
- *Texture*.—Glabrous.

FLOWER

Natural flowering season: July to August.

Inflorescence and flower type and habit: Compound umbel. Terminal clusters of salverform flowers.

Inflorescence:

- *Diameter*.—6 cm.
- *Height*.—5 cm.
- *Flowers per inflorescence*.—15 to 20.
- *Flowers and buds per plant*.—600 to 900. Each lateral branch has at least one terminal inflorescence. Each terminal inflorescence has 15 to 20 flowers and 5 to 10 buds. Plants have on average 30 lateral branches.

Individual flower:

- *Type/form*.—Salverform.
- *Habit*.—Terminally.
- *Persistence*.—Self-cleaning.
- *Fragrance*.—None.
- *Aspect*.—Upright.
- *Diameter*.—1.75 cm.
- *Length/depth*.—2.5 cm.

*Tube length.*—2.25 cm.
*Throat diameter, proximal end.*—4 mm.
*Throat diameter, distal end.*—2.5 mm.

Bud:
*Shape.*—Oblong, flaring to triangular at tip.
*Length.*—2 cm.
*Diameter.*—3 mm.
*Color.*—RHS Red 43A.

Petals:
*Quantity.*—4.
*Arrangement.*—Cruciform; 4 petals arranged in a whorl around throat opening.
*Length from throat.*—8 mm.
*Corolla lobe attitude.*—Semi-erect.
*Width.*—5 mm.
*Shape.*—Ovate.
*Apex.*—Acute.
*Base.*—Fused.
*Margin.*—Entire.
*Texture.*—Smooth and silky, both sides.
*Color.*—When Opening, Upper Surface: RHS Red 44B. When Opening, Lower Surface: RHS Red 43A. Fully Opened, Upper Surface: RHS Red 44B. Fully Opened, Lower Surface: RHS Red 43A.
*Tube color.*—RHS Red 43A with a small band of Red-Purple 69D at the base.
*Tube texture.*—Smooth; soft, velvety pubescence.
*Throat color.*—RHS Red 43A.
*Throat texture.*—Smooth; soft, velvety pubescence.

Sepals:
*Arrangement.*—Whorl around base.
*Appearance.*—Thin and acicular.
*Quantity.*—4.
*Length.*—4 mm.
*Width.*—1 mm.
*Shape.*—Acicular.
*Margin.*—Entire.
*Apex.*—Acute.
*Base.*—Fused.
*Color.*—Upper Side: RHS Green 138A to 138B. Under Side: RHS Green 138A to 138B.
*Texture.*—Upper side: Smooth, soft, velvety pubescence. Lower side: Smooth, soft, velvety pubescence.
*Calyx shape.*—Collar-like.

Peduncles:
*Length.*—1 cm.
*Diameter.*—2 mm.
*Angle.*—45° to stem.
*Strength.*—Good.
*Texture.*—Glabrous.
*Color.*—RHS Yellow-Green 146C.

Pedicels:
*Length.*—4 mm.
*Diameter.*—1 mm.
*Angle.*—45° to peduncle.
*Strength.*—Good.
*Texture.*—Very slightly pubescent.
*Color.*—RHS Yellow-Green 146C.

REPRODUCTIVE ORGANS

Stamens:
*Number.*—4.
*Filament length.*—2 mm.
*Filament color.*—RHS White NN155C.

Anthers:
*Shape.*—Linear.
*Petaloidy.*—Absent.
*Length.*—2 mm.
*Color.*—RHS Greyed-Yellow 161C.
*Pollen color.*—RHS Greyed-Yellow 161C.
*Pollen amount.*—Sparse to fair.

Pistil:
*Number.*—1.
*Length.*—1.5 cm.
*Style.*—Length: 1.25 cm. Color: RHS White NN155A.
*Stigma.*—Shape: 2 linear/oblong lobes. Color: RHS Greyed-Red 182A. Ovary Color: RHS Green 138B.

OTHER CHARACTERISTICS

Seeds: Not observed.
Disease/pest resistance: Neither resistance nor susceptibility to normal diseases and pests of *Bouvardia* observed.
Temperature tolerance: Low temperature tolerance to −12° C., high temperature tolerance to at least 30° C.

What is claimed is:

1. A new and distinct cultivar of *Bouvardia* plant named 'WNBVESRED24' as herein illustrated and described.

* * * * *